United States Patent
Tseng et al.

(10) Patent No.: US 8,501,428 B2
(45) Date of Patent: Aug. 6, 2013

(54) SINGLE MOLECULE DETECTION PLATFORM, MANUFACTURING METHOD THEREOF AND METHOD USING THE SAME

(75) Inventors: Fan Gang Tseng, Hsinchu (TW); Sheng Hsun Wu, Hsinchu (TW); Ming Hung Chen, Kaohsiung County (TW)

(73) Assignee: National Tsing Hua University, Hsinchu (TW)

( * ) Notice: Subject to any disclaimer, the term of this patent is extended or adjusted under 35 U.S.C. 154(b) by 330 days.

(21) Appl. No.: 12/944,151

(22) Filed: Nov. 11, 2010

(65) Prior Publication Data

US 2011/0117587 A1    May 19, 2011

(30) Foreign Application Priority Data

Nov. 13, 2009  (TW) ............................... 98138545 A

(51) Int. Cl.
*C12Q 1/66* (2006.01)
*C12Q 1/42* (2006.01)
*G01N 21/64* (2006.01)

(52) U.S. Cl.
USPC ............................... 435/8; 435/288.7; 435/21

(58) Field of Classification Search
None
See application file for complete search history.

(56) References Cited

U.S. PATENT DOCUMENTS 7,267,948 B2    9/2007   Vo-Dinh
2009/0274873 A1*  11/2009  Shinotsuka ................... 428/143

OTHER PUBLICATIONS

Office Action of TW counterpart application No. 098138545 dated Aug. 29, 2012.
English abstract of Office Action of TW counterpart application No. 098138545 dated Aug. 29, 2012.

* cited by examiner

*Primary Examiner* — Jon P Weber
*Assistant Examiner* — Charles Zoltan Constantine
(74) *Attorney, Agent, or Firm* — WPAT, P.C.; Anthony King

(57) ABSTRACT

A single molecule detection platform is disclosed. The single molecule detection platform comprises a light-transmissive substrate, a plurality of spherical particles and a thin film. The surface of the light-transmissive substrate is etched to form a plurality of cone-shaped structures. Each spherical particle is disposed on top of each cone-shaped structure. The sizes of the plurality of spherical particles are suitable to allow only a single protein to be attached to each spherical particle. The thin film is deposited on the surface of the plurality of cone-shaped structures and acts as a reflective layer of one-dimensional waveguide. The plurality of spherical particles is not covered by the thin film.

39 Claims, 5 Drawing Sheets

SINGLE MOLECULE DETECTION PLATFORM, MANUFACTURING METHOD THEREOF AND METHOD USING THE SAME

BACKGROUND OF THE INVENTION

1. Field of the Invention

The present invention relates to a single molecule detection technique, and more particularly, to a single molecule detection platform, the manufacturing method thereof and the method using the same.

2. Description of the Related Art

Enzymes are catalysts existing in organisms for performing a variety of crucial tasks and functions. Much scientific research focuses on the structure and functions of enzymes. For centuries, most observations of enzymes have been obtained by taking whole-scale measurements of very large amounts of bio-molecules. However, such measurements fail to provide reaction kinetics of single molecules.

Recently, nanotechnology has become one of the most important fields of research. From high-tech industries to ordinary consumer apparatuses, applications of nanotechnology can be seen almost everywhere. Nanotechnology can be applied to a variety of fields, such as the basic science research or applied science research, including biology, pharmacy, physics, chemistry, material engineering and optical engineering. Nanostructures can also be found in nature, such as the epidermal cells of the lotus leaf that exhibits the lotus effect, or all kinds of insects with nanometer-scaled magnetic particles inside their bodies.

Recently, single-molecule nanotechnology that integrates biology and nanotechnology has been widely utilized and is expected to overcome the issues of performing whole-scale measurements, and accordingly provides an opportunity for starting a new era of biology. Such technology allows researchers to study the reaction behavior of single molecules in real time. However, although current development of single-molecule nanotechnology provides methods to study the characteristics of single molecules, most of those methods are realized by controlling the sample concentration and monitoring the reactions among a vast number of bio-molecules. Accordingly, even if observing large quantities of samples, researchers can only obtain limited information. In addition, additional statistics are required to clarify the ambiguities of the single molecule reaction.

Take, for example, a design experiment for the mutual reaction between an enzyme and a substrate. Such design experiment uses enzyme-containing grooves of 50 nanometers to limit the contact between the enzyme and substrate such that the reaction probability of the enzyme and substrate is reduced. Such design experiment improves the detection concentration of the substrate a thousand times compared to the conventional methods. In addition, the limited volume of the grooves is helpful for the excitation of the local fluorescence of the reaction. However, such design experiment suffers from several drawbacks:

1. The single-molecule reaction between a single enzyme and substrate is not guaranteed. In other words, the probability of the occurrence of the single molecule reaction ranges from one in a hundred to one in ten thousand, and thus total control is difficult to achieve. If the mutual reaction between the enzyme and substrate takes two or three steps, such drawback becomes more significant.

2. To clarify the ambiguities of the single-molecule reaction, countable statistics, which require large amounts of experiment data and time, are required.

3. If the concentration of the substrate is low, it may take too long for the single-molecule reaction to occur. This drawback may greatly reduce the probability of the second and the third steps of the reaction between the enzyme and substrate, and results in the limitation of the capability for measuring the reaction kinetics of the enzyme.

4. To maintain a reasonable reaction probability and detection time, the range of the substrate concentration must be controlled within one or two orders.

Accordingly, there is a need for a system and method that can overcome the aforementioned drawbacks and can increase the range of the molecule reaction kinetics, reduce background noise, increase the controllability of local substrate concentration, and reduce the range of the excitation signal.

SUMMARY OF THE INVENTION

The single molecule detection platform according to one embodiment of the present invention comprises a light-transmissive substrate, a plurality of spherical particles, and a thin film. The surface of the light-transmissive substrate is etched to form a plurality of cone-shaped structures. Each of the plurality of spherical particles is disposed on the top of one cone-shaped structure, wherein the sizes of the plurality of spherical particles are suitable to allow a single protein to be attached to each of the spherical particles. The thin film is deposited on the surface of the plurality of cone-shaped structures and acts as a reflective layer of a one-dimensional waveguide.

The manufacturing method for a single molecule detection platform according to one embodiment of the present invention comprises the steps of: disposing a plurality of spherical particles on a light-transmissive substrate; etching the light-transmissive substrate by using the plurality of spherical particles as masks to form a plurality of cone-shaped structures on the surface of the light-transmissive substrate; and depositing a thin film on the surface of the plurality of cone-shaped structures, wherein the plurality of spherical particles do not remain covered by the thin film.

The detection method using a single molecule detection platform provided by the embodiments of the present invention according to one embodiment of the present invention comprises the steps of: rendering reactions between a plurality of substrates and the enzymes attached to the plurality of spherical particles by flowing a fluid containing the plurality of substrates over the plurality of spherical particles; and emitting laser beams on the bottom of the light-transmissive substrate to excite fluorescence and generate fluorescent spots on the top of the plurality of spherical particles.

The foregoing has outlined rather broadly the features and technical advantages of the present invention in order that the detailed description of the invention that follows may be better understood. Additional features and advantages of the invention will be described hereinafter, and form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The objectives and advantages of the present invention will become apparent upon reading the following description and upon referring to the accompanying drawings of which.

DETAILED DESCRIPTION OF THE INVENTION

Figure 1:
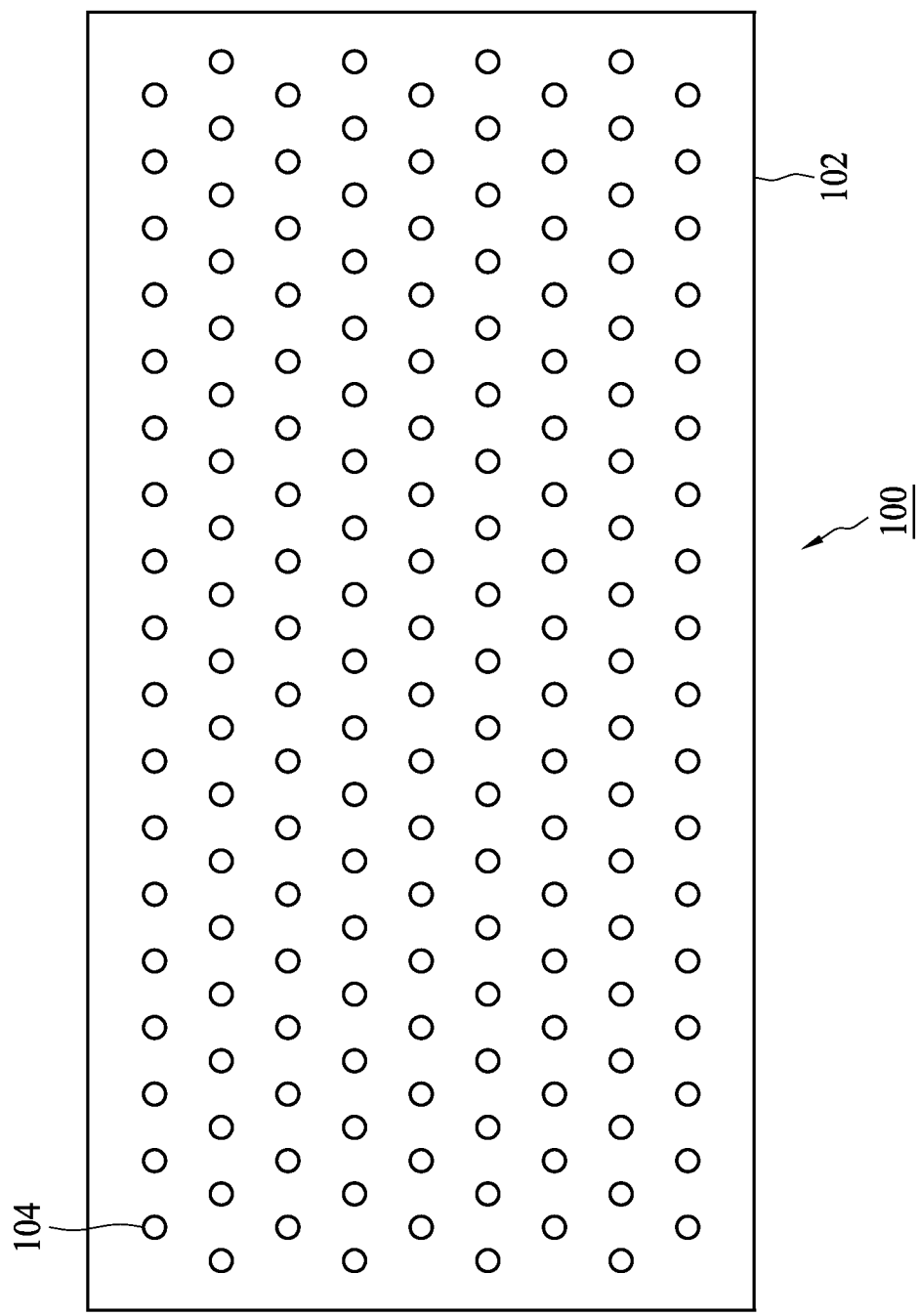
FIG. 1 shows a single molecule detection platform according to one embodiment of the present invention.

FIG. 1 shows a single molecule detection platform according to one embodiment of the present invention. As shown in FIG. 1, the single molecule detection platform 100 comprises a substrate 102 and a plurality of spherical particles 104. The substrate 102 is a light-transmissive substrate, and is made of fused silica. The surface of the substrate 102 is etched to form a plurality of cone-shaped structures, wherein the plurality of cone-shaped structures is arranged in a hexagonal-close manner.

Figure 2:
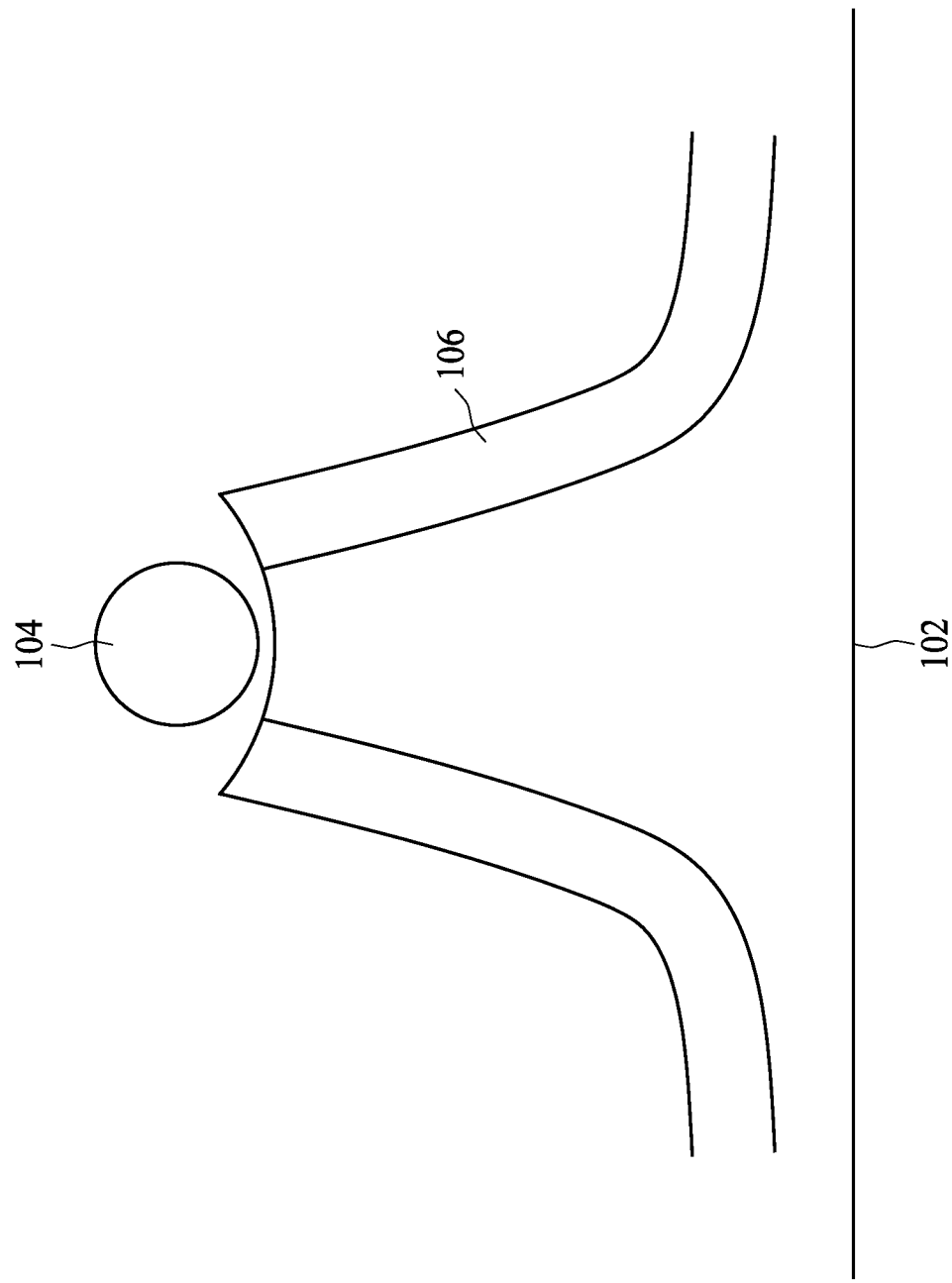
FIG. 2 shows the partial schematic of a single molecule detection platform according to one embodiment of the present invention.

FIG. 2 shows the partial schematic of the single molecule detection platform 100 shown in FIG. 1. As shown in FIG. 2, the spherical particle 104 is made of metal, e.g. gold, and is disposed on the top of one of the cone-shaped structures. The size of the spherical particle 104 allows a single enzyme to be attached to the surface of a single spherical particle 104. The surface of the cone-shaped structure is covered by a thin film 106 made of aluminum, wherein the spherical particle 104 are not covered by the thin film 106. The thin film 106 acts as a reflective layer of a one-dimensional waveguide.

In one embodiment of the present invention, each of the plurality of spherical particles 104 is linked to a fluorescent-marked protein via one or more thiol molecules. Accordingly, the single molecule detection platform 100 includes the plurality of spherical particles 104, each of which is linked to a fluorescent-marked protein. Such architecture can be applied to fluorescence detection of single molecule reaction in a large scale.

Figure 3:
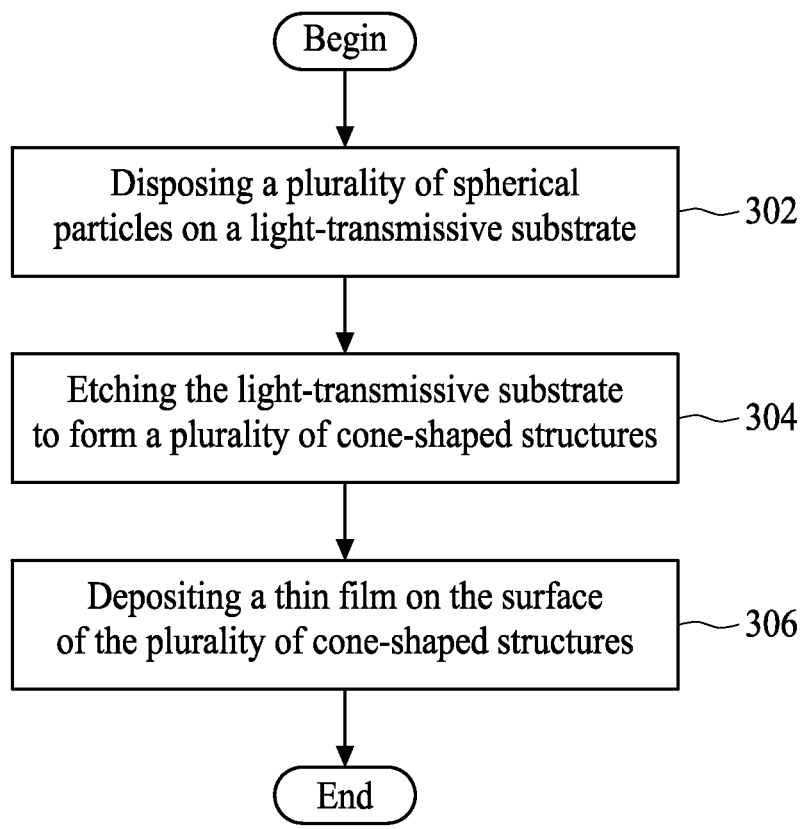
FIG. 3 shows the flowchart of a manufacturing method for a single molecule detection platform according to one embodiment of the present invention.

FIG. 3 shows the flowchart of a manufacturing method for a single molecule detection platform according to one embodiment of the present invention. In step 302, a plurality of spherical particles is disposed on a light-transmissive substrate, and step 304 is executed. In step 304, the light-transmissive substrate is etched by using the plurality of spherical particles as masks to form a plurality of cone-shaped structures on the surface of the light-transmissive substrate, and step 306 is executed. In step 306, a thin film is deposited on the surface of the plurality of cone-shaped structures and the plurality of spherical particles do not remain covered by the thin film.

In one embodiment of the present invention, step 302 is carried out as follows. First, a substrate made of fused silica is provided. Second, a plurality of polystyrene beads is spin coated on the surface of the substrate in a hexagonal-close manner, wherein the diameters of the plurality of polystyrene beads range from 400 nanometers to 1000 nanometers. Third, the gap between polystyrene beads is increased by temporarily using oxygen plasma. Fourth, an E-gun evaporation technique is utilized to deposit metal, e.g. gold, at the gaps between polystyrene beads. Fifth, the plurality of polystyrene beads is removed. Finally, an annealing procedure is performed to shrink the plurality of metal deposits to form a plurality of spherical particles, wherein the diameters of the plurality of spherical particles range from 20 nanometers to 40 nanometers.

In one embodiment of the present invention, step 304 is carried out as follows. A reactive ion etching procedure is performed on the substrate, wherein the plurality of spherical particles act as masks. The reactive ion etching procedure uses $CF_4$ and $O_2$ as the etching air, and a total of four circulations are performed. It should be noted that by changing the ratio between $CF_4$ and $O_2$, the sizes and shapes of the plurality of cone-shaped structures and the plurality of spherical particles can be controlled. In this embodiment, the ratio between $CF_4$ and $O_2$ gradually changes from 10:5 to 5:10. After the etching procedure is complete, the diameters of the plurality of spherical particles range from 4 nanometers to 10 nanometers, wherein the surface area of the top of each of the plurality of cone-shaped structures is greater than the cross-sectional area of each of the plurality of spherical particles.

In one embodiment of the present invention, step 306 is carried out as follows. First, an E-gun evaporation technique is utilized to deposit aluminum on the surface of the substrate. Second, an annealing procedure is performed to expose the plurality of spherical particles through the thin film.

Figure 4:
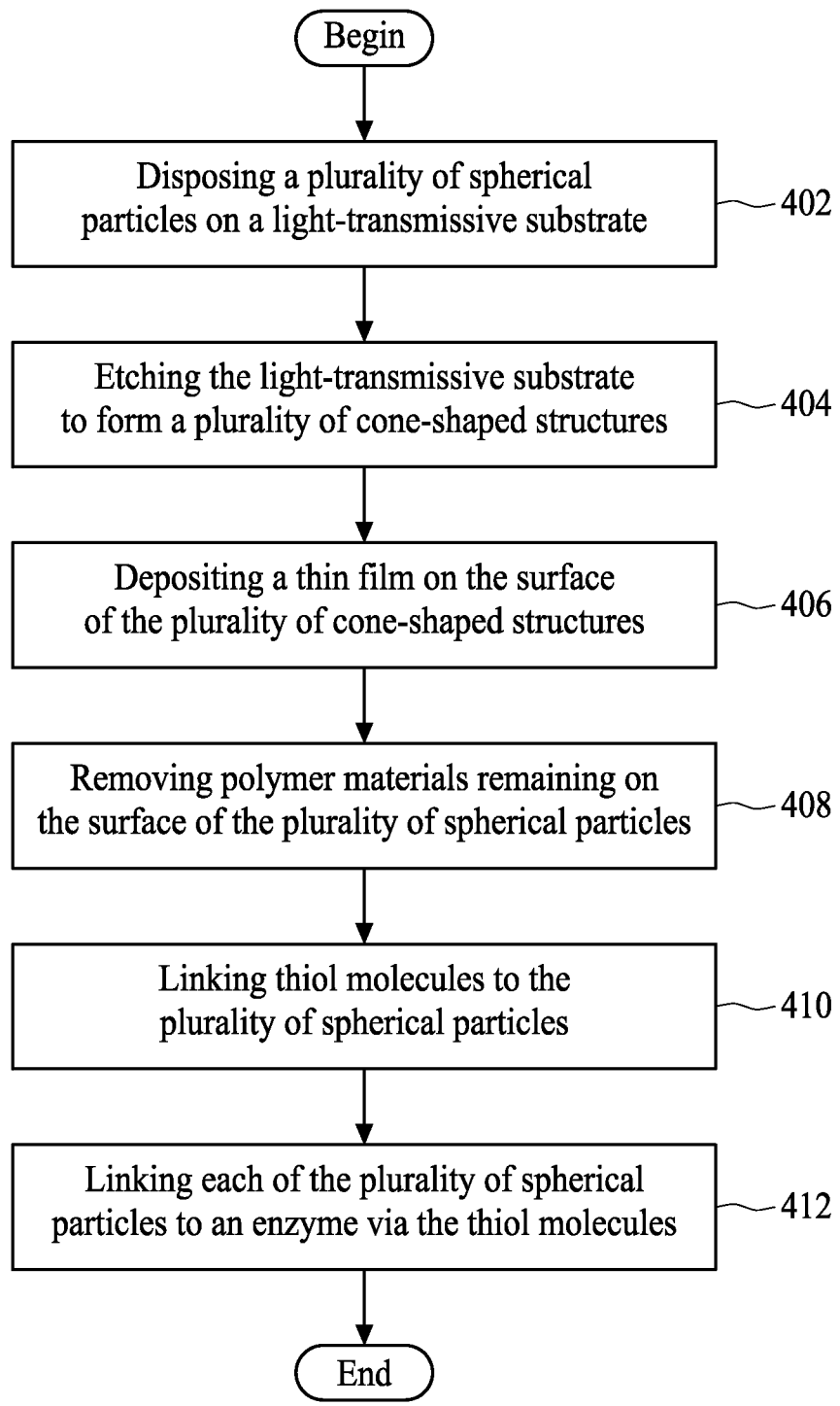
FIG. 4 shows the flowchart of a manufacturing method for a single molecule detection platform according to another embodiment of the present invention.

FIG. 4 shows the flowchart of a manufacturing method for a single molecule detection platform according to another embodiment of the present invention. As shown in FIG. 4, steps 402 to 406 are similar to steps 302 to 306. In step 408, the polymer materials remaining on the surface of the plurality of spherical particles are removed, and step 410 is executed. In step 410, thiol molecules are linked to the surface of the plurality of spherical particles, and step 412 is executed. In step 412, each of the plurality of spherical particles is linked to a protein molecule via the thiol molecules.

In one embodiment of the present invention, step 408 is carried out by using oxygen plasma or a soaking procedure to remove the remaining polymer materials. In another embodiment of the present invention, these thiol molecules are thiol molecules with amino or COOH functional groups. In yet another embodiment of the present invention, these protein molecules are fluorescent-marked protein molecules or luciferases, wherein the fluorescence is the fluorescence of Cy3.

Figure 5:
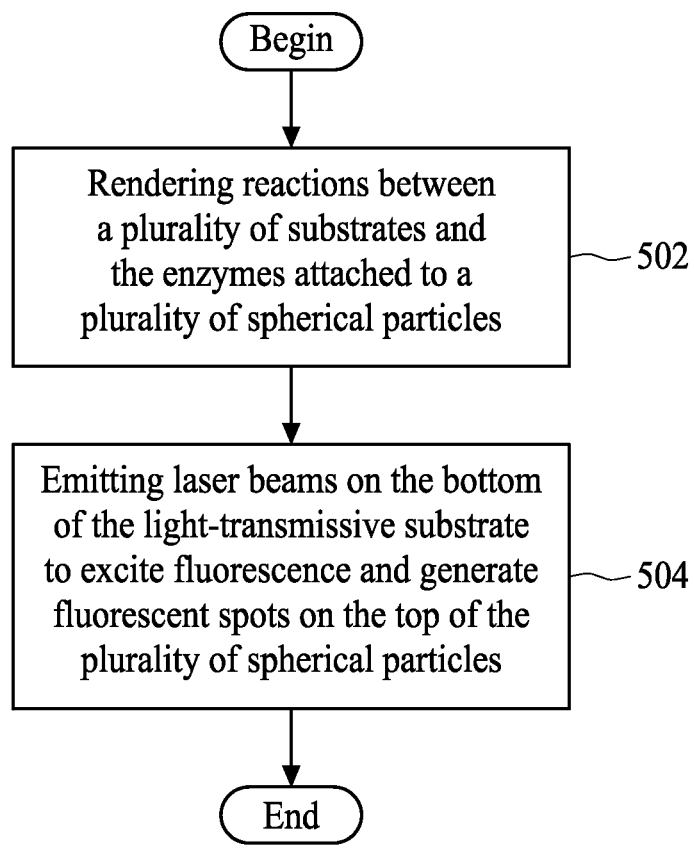
FIG. 5 shows the flowchart of a detection method using a single molecule detection platform according to one embodiment of the present invention.

FIG. 5 shows the flowchart of a detection method using a single molecule detection platform according to one embodiment of the present invention, wherein the single molecule detection platform is provided by the present invention. In step 502, reactions between a plurality of substrates and the enzymes attached to the plurality of spherical particles are rendered by flowing a fluid containing the plurality of substrates over the plurality of spherical particles, and step 504 is executed. In step 504, laser beams are emitted on the bottom of the light-transmissive substrate to excite fluorescence and generate fluorescent spots on the top of the plurality of spherical particles.

In one embodiment of the present invention, step 502 is carried out by using an alternative current electro-osmosis flow (AC EOF) apparatus to flow the fluid over the plurality of spherical particles such that the reactions between the plurality of substrates and the enzymes can occur. In another embodiment of the present invention, the incident laser beams propagate through a one-dimensional waveguide of the aluminum thin film to the top of the plurality of spherical particles to generate fluorescent spots with diameters under 100 nanometers. In yet another embodiment of the present invention, the concentration of the plurality of substrates in the fluid ranges from 1 μM to 1 fM, and the time interval of the flowing of the fluid ranges from 100 microseconds to 100 milliseconds. In yet another embodiment of the present invention, the excited fluorescence is filtered by an optical filter, and is received by a sensitive TE cooling charge-coupled device to produce images.

In another embodiment of the present invention, a finite difference time domain algorithm can be used to calculate the transmittance of the incident laser beams and the distribution of the incident laser beams within the plurality of cone-shaped structures. In yet another embodiment of the present invention, a near-field optical lithography technique can be performed to measure the relation between the plurality of cone-shaped structures and the plurality of spherical particles versus the near-field optical distribution, wherein the near-field optical lithography technique is performed by coating a photosensitive thin film on the light-transmissive substrate and capturing the near-field optical distribution by using a near-field scanning optical microscope.

In conclusion, the single molecule detection platform, the manufacturing method thereof and the method using the same provided by the present invention are focused on the detection of single molecule reactions without gathering a large amount of statistics. For example, the method provided by the present invention can detect the reaction between H+ and PPase. As shown in the aforementioned embodiments, researchers can describe the reaction of a single bio-molecule in detail, or precisely obtain the distance a single bio-molecule travels in microseconds in nanometer scale. Furthermore, by applying the aforementioned embodiments, researchers can overcome the problem of directly and simultaneously observing huge and complex cell reactions.

Although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A single molecule detection platform, comprising:
   a light-transmissive substrate, the surface of which has been etched to form a plurality of cone-shaped structures;
   a plurality of spherical particles, each of which is disposed on the top of each cone-shaped structure, wherein the sizes of the plurality of spherical particles are suitable to allow a single protein to be attached to each of the spherical particles; and
   a thin film, deposited on the surface of the plurality of cone-shaped structures and acting as a reflective layer of a one-dimensional waveguide;
   wherein the plurality of spherical particles is not covered by the thin film.

2. The single molecule detection platform of claim 1, wherein the light-transmissive substrate is made of fused silica.

3. The single molecule detection platform of claim 1, wherein the plurality of spherical particles are made of metal.

4. The single molecule detection platform of claim 1, wherein the diameter of each of the plurality of spherical particles ranges from four nanometers to ten nanometers.

5. The single molecule detection platform of claim 1, wherein the plurality of cone-shaped structures is arranged in a hexagonal-close manner.

6. The single molecule detection platform of claim 1, wherein the surface area of the top of each of the plurality of cone-shaped structures is greater than the cross-sectional area of each of the plurality of spherical particles.

7. The single molecule detection platform of claim 1, wherein the thin film is made of aluminum.

8. The single molecule detection platform of claim 1, wherein each of the plurality of spherical particles is linked to a luciferase.

9. The single molecule detection platform of claim 8, wherein each of the plurality of spherical particles is linked to a luciferase via one or more thiol-containing molecules.

10. The single molecule detection platform of claim 9, wherein the luciferase is labeled with a fluorescent dye.

11. The single molecule detection platform of claim 1, wherein an enzyme is linked to each of the plurality of spherical particles.

12. The single molecule detection platform of claim 11, wherein the enzyme is labeled with a fluorescent dye.

13. A manufacturing method for a single molecule detection platform, comprising the steps of:
   disposing a plurality of spherical particles on a light-transmissive substrate;
   etching the light-transmissive substrate to form a plurality of cone-shaped structures on the surface of the light-transmissive substrate, wherein the plurality of spherical particles act as masks during the etching; and
   depositing a thin film on the surface of the plurality of cone-shaped structures, and
   performing an annealing procedure to expose the plurality of spherical particles through the thin film.

14. The manufacturing method of claim 13, wherein the step of disposing a plurality of spherical particles comprises the sub-steps of:
   spin coating a plurality of polystyrene beads on the surface of the light-transmissive substrate;
   depositing a material in the gap between polystyrene beads by an evaporation process;
   removing the plurality of polystyrene beads; and
   performing an annealing process to form the plurality of spherical particles from the deposited material.

15. The manufacturing method of claim 14, wherein the light-transmissive substrate is made of fused silica.

16. The manufacturing method of claim 14, wherein the diameters of the plurality of polystyrene beads range from 400 nanometers to 1000 nanometers.

17. The manufacturing method of claim 13, wherein the plurality of spherical particles are made of metal.

18. The manufacturing method of claim 13, wherein the plurality of spherical particles are arranged in a hexagonal-close manner.

19. The manufacturing method of claim 13, wherein the diameters of the plurality of spherical particles before the etching step range from 20 nanometers to 40 nanometers.

20. The manufacturing method of claim 13, wherein the diameters of the plurality of spherical particles after the etching step range from 4 nanometers to 10 nanometers.

21. The manufacturing method of claim 13, wherein the etching step is realized by performing a dry etching process.

22. The manufacturing method of claim 21, wherein the etching step is realized by performing a reactive ion etching process.

23. The manufacturing method of claim 22, wherein the reactive ion etching process uses $CF_4$ and $O_2$ as the main gas.

24. The manufacturing method of claim 23, wherein the reactive ion etching process is performed through four circulations.

25. The manufacturing method of claim 24, wherein in the reactive ion etching process, the ratio between $CF_4$ and $O_2$ gradually changes from 10:5 to 5:10.

26. The manufacturing method of claim 13, wherein the depositing comprises
evaporating the thin film onto the surface of the light-transmissive substrate.

27. The manufacturing method of claim 13, further comprising the steps of:
linking thiol-containing molecules to the plurality of spherical particles; and
linking an enzyme to each of the plurality of spherical particles via the thiol-containing molecules.

28. The manufacturing method of claim 27, wherein the thiol-containing
molecules further comprise amino or carboxylic functional groups.

29. The manufacturing method of claim 27, wherein the enzyme is luciferase.

30. The manufacturing method of claim 29, wherein luciferase is labeled with fluorescence dye.

31. A method of detecting with the
the single molecule detection platform of claim 12 comprising the steps of:
catalyzing a reaction of a substrate with the enzyme attached to the plurality of spherical particles by flowing a fluid containing the substrate over the plurality of spherical particles;
emitting laser beams on the bottom of the light-transmissive
substrate to excite fluorescence of the labeled enzyme and generate fluorescent spots on the top of
the plurality of spherical particles; and
imagining the fluorescent spots.

32. The detection method of claim 31, wherein an alternative current electro-osmosis flow apparatus is utilized to flow the fluid over the plurality of spherical particles.

33. The detection method of claim 31, wherein the diameters of the fluorescent spots are smaller than 100 nanometers.

34. The detection method of claim 31, wherein the concentration of the substrate in the fluid ranges from 1 µM to 1 fM.

35. The detection method of claim 31, wherein the time interval of the flowing of the fluid ranges from 100 microseconds to 100 milliseconds.

36. The detection method of claim 31, wherein the excited fluorescence is filtered by an optical filter, and is received by a cooling charge-coupled device to produce images.

37. The detection method of claim 31, further comprising the steps of:
calculating the transmittance of the incident laser beams and the distribution of the incident laser beams within the plurality of cone-shaped structures by a finite-difference time-domain algorithm; and
measuring the relation between the plurality of cone-shaped structures and the plurality of spherical particles versus the near-field optical distribution by performing a near-field optical lithography technique.

38. The detection method of claim 37, wherein the near-field optical lithography technique is performed by coating a photosensitive thin film on the light-transmissive substrate and capturing the near-field optical distribution by using a near-field scanning optical microscope.

39. The detection method of claim 31, wherein the enzyme is a phosphatase.

* * * * *